United States Patent [19]
von Zeppelin

[11] Patent Number: 4,971,055
[45] Date of Patent: Nov. 20, 1990

[54] BLOOD VESSEL CLAMP

[76] Inventor: Dieter von Zeppelin, Wittelsbacher Str. 20, D-8000 Munich 5, Fed. Rep. of Germany

[21] Appl. No.: 218,108

[22] Filed: Jul. 12, 1988

[30] Foreign Application Priority Data

Jul. 14, 1987 [DE] Fed. Rep. of Germany ....... 3723167

[51] Int. Cl.⁵ .............................................. A61B 17/12
[52] U.S. Cl. ..................................... 606/158; 24/500
[58] Field of Search ............... 128/321, 354, 325, 346, 128/322; D24/27; 24/499, 500, 501, 502

[56] References Cited

U.S. PATENT DOCUMENTS

| | | | |
|---|---|---|---|
| 3,802,437 | 4/1974 | Kees | 128/325 |
| 3,805,792 | 4/1974 | Cogley | 128/325 |

FOREIGN PATENT DOCUMENTS 105414 4/1984 European Pat. Off. ............ 128/325

Primary Examiner—Michael H. Thaler
Attorney, Agent, or Firm—Harness, Dickey & Pierce

[57] ABSTRACT

A clamp for pinching off a blood vessel or aneurysm comprises a pair of arms pivotally attached at the center and crossing over one another so that opposing hemostatic ends at one end of the arms are open by opening the operational ends at the other ends of the arms, the operational ends of the clamp being grasped by an applying instrument through buttons or recesses on an inwardly directed portion of the operational ends to reduce visual obstruction in the area in which the clamp is used.

10 Claims, 6 Drawing Sheets

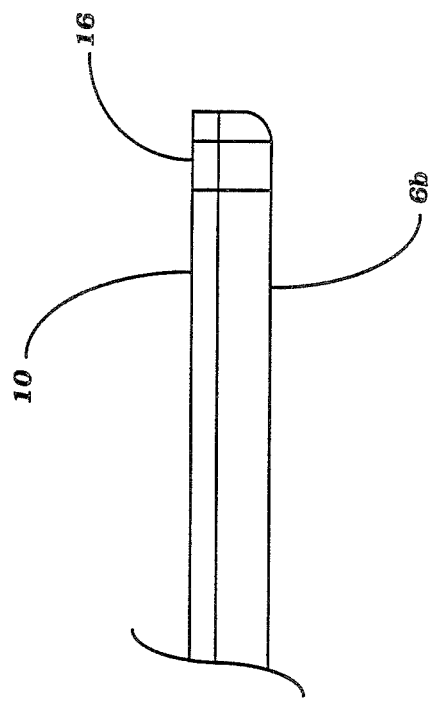

4,971,055

BLOOD VESSEL CLAMP

FIELD OF THE INVENTION

The present invention pertains to surgical procedures in which a blood vessel or aneurysm must be blocked by pinching off the vessel with a device, either temporarily or permanently, to prevent bleeding or hemorrhaging.

BACKGROUND OF THE INVENTION

In surgery, and in particular microsurgery techniques, blood vessels, aneurysms and the like, often must be clamped to prevent bleeding and hemorrhaging in very narrow special surroundings. The problem is a particularly burdensome one when clamping deep-lying, craneal aneurysms due to the fact that space and visibility is severely limited by surrounding brain tissue.

Clamps utilized for clamping blood vessels and aneurysms have heretofore generally had a configuration in which the clamp or an end of the clamp is grasped by forceps and squeezed to open the hemostatic end of the clamp for application to a blood vessel. The handling of the clamp by forceps from outside partially conceals the clamp and positions the forceps to substantially obstruct visibility of the clamp and the blood vessel or aneurysm to which the clamp is being applied.

With a clamp configuration in which the clamp is operated by squeezing a portion of the clamp with a pair of forceps, to assure the clamp is not dropped during application, paricularly with difficult reaches, the forceps used for applying the clamp generally must have a shaped end portion which captures the clamp. Some designs have even used interlocking means such as a pin which is formed at the tip of the forceps which fits in a corresponding hole formed in the portion of the clamp wherein the clamp is held thereby. This requires the ends of the forceps used for application to be enlarged which further obstructs visibility of the area in which the clamp is being utilized.

Blood vessel and aneurysm clamps have been constructed in two general configurations. In the first the arms of the clamp are pivotally attached to one another at a central location and do not cross over one another so that when the operational end of the clamp is squeezed together the hemostatic end of the clamp opens. The second type of clamp is a one piece construction of spring steel in which the hemostatic ends of the clamp cross over one another so that as the spring expands outwardly the hemostatic ends are closed together. This type of clamp is operated by squeezing the spring portion to open the hemostatic ends. In both of these clamp types the forceps used for application must engage the clamp from outside thereby resulting in the visible obstruction as discussed above.

There exists a need for a blood vessel or aneurysm clamp which can be applied in a manner and through use of an instrument which substantially reduces visual obstruction of the area in which the clamp is being utilized. It is toward this objective which the invention presented herein is directed.

SUMMARY OF THE INVENTION

A clamp for pinching off a blood vessel or aneurysm is presented which is operated by spreading out the operational ends thereof to open hemostatic ends of the clamp for application. It is possible to grasp the clamp with an application instrument from within the operational ends of the clamp, thereby substantially reducing visual obstruction in the area in which the clamp is utilized. Visual effectiveness is improved since the application instrument engages the clamp from within its structure, rather than grasping the clamp from outside, thus reducing the size of the clamp and instrument combination. Furthermore, this construction substantially improves visibility of the hemostatic portion of the clamp at the vessel or aneurysm during application.

DESCRIPTION OF THE DRAWINGS

FIG. 7 is a cutaway fragmentary side view of the operational end of another embodiment of a blood vessel or aneurysm clamp as described herein.

DETAILED DESCRIPTION OF THE INVENTION

Figure 1:
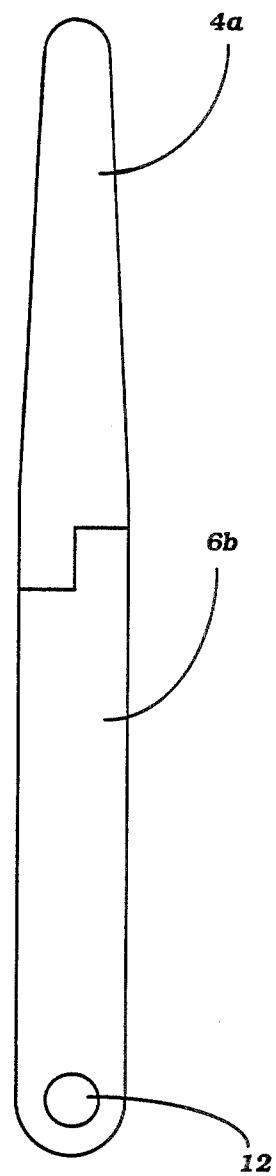
FIG. 1 is a top view of a blood vessel or aneurysm clamp as described herein.
Figure 2:
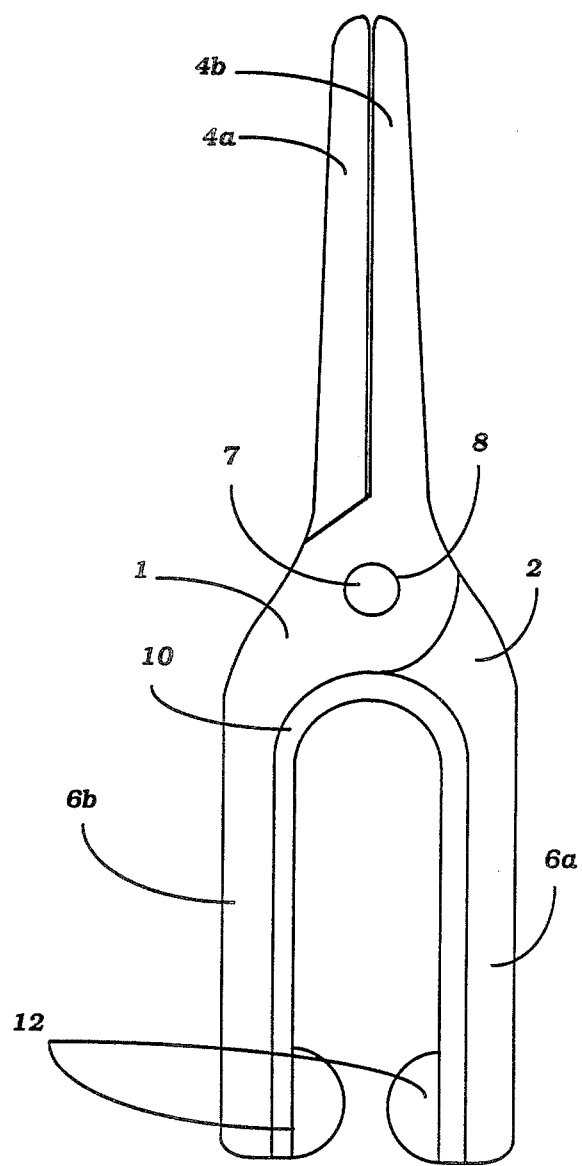
FIG. 2 is a side view of a blood vessel or aneurysm clamp as described herein.

A blood vessel or aneurysm clamp is shown in FIGS. 1 and 2 which comprises a pair of arms, generally identified as 1 and 2, each of which has a hemostatic end 4a, 4b respectively, and an operational end 6a, 6b respectively. The arms 1 and 2 are shaped to be assembled by a pin 7, which extends through bores 8 formed in a central portion of each of the arms 1 and 2 to provide pivotal movement there between. Each of the arms 1 and 2 is shaped in a mirror image fashion so when they are assembled they cross over one another with the hemostatic ends 4a, 4b for each arm aligning with and opposing one another to provide opposing clamping surfaces. The operational ends 6a and 6b also align with and oppose one another. A spring 10 is provided, which is shown as a u-shaped leaf spring to urge the hemostatic ends 4a, 4b of the arms 1 and 2 against one another. Spring 10 is preferably positioned within the operational ends 6a and 6b of the arms 1 and 2 to bias the operational ends inwardly, thus applying force through the pin 7 on which the arms pivot to close the hemostatic ends 4a, 4b. The spring is sized to provide a select closing force at the hemostatic ends 4a, 4b of the clamp.

Pins or rivets 12 are provided at the inside outer portions of the operational ends 6a, 6b of each of the arms 1 and 2 which can be engaged by an applying instrument to securely hold the clamp during an application procedure. The application instrument thus engages the operational ends 6a, 6b of the arms 1 and 2 from in between them and moves them outwardly to open the hemostatic ends 4a, 4b. Since the applying instrument grasps the operational ends of the clamp from the inside through the pins or rivets 12 and not from outside, there is substantially reduced visual obstruction when applying a clamp to a blood vessel or aneurysm. If rivets 12 are utilized they may additionally retain the spring 10 within the operational ends 6a, 6b of the arms 1 and 2 by attaching each of the ends of the spring 10 respectively to the outer portions of the operational ends of the arm 1 and 2.

Figure 4:
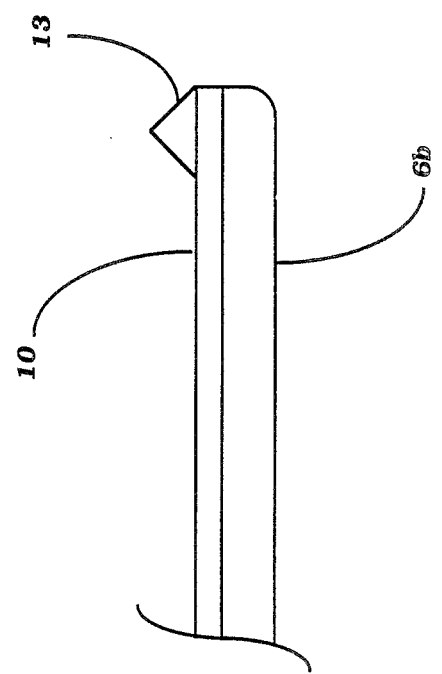
FIG. 4 is a fragmentary side view of the operational end of another embodiment of a blood vessel or aneurysm clamp as described herein.
Figure 5:
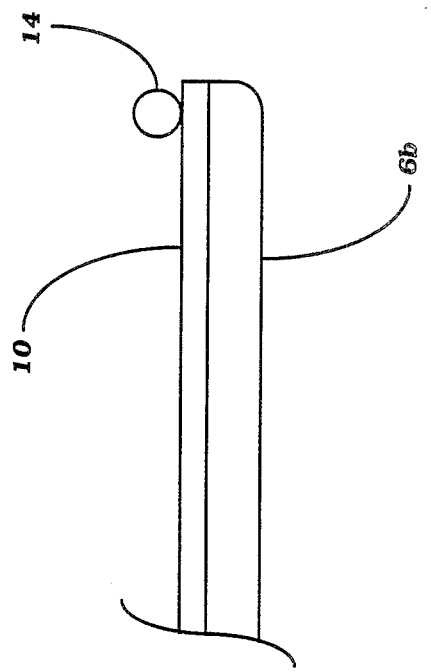
FIG. 5 is a fragmentary side view of the operational end of another embodiment of a blood vessel or aneurysm clamp as described herein.
Figure 6:
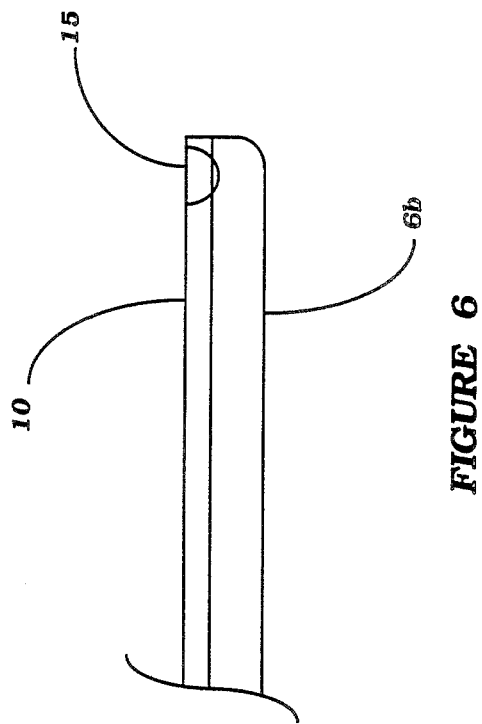
FIG. 6 is a cutaway fragmentary side view of the operational end of another embodiment of a blood vessel or aneurysm clamp as described herein.

If pins 12 are utilized, they may have a cylindrical, pyramid 13 as shown in FIG. 4, semispherical or spherical shape 14 as shown in FIG. 5, or other shape which permits rotational movement of the clamp with the applying instrument when held thereby. Alternatively recesses 15 as shown in FIG. 6 or bores 16 as shown in FIG. 7 may be formed in the outward portion of the operational ends 6a and 6b of arms 1 and 2 to receive cooperating shape elements on the applying instrument. It is thus possible for the applying instrument to hold the clamp in different rotational angles to the applying instrument which permits varying attitudes of the clamp therewith for application of the clamp in congested areas.

Figure 3:
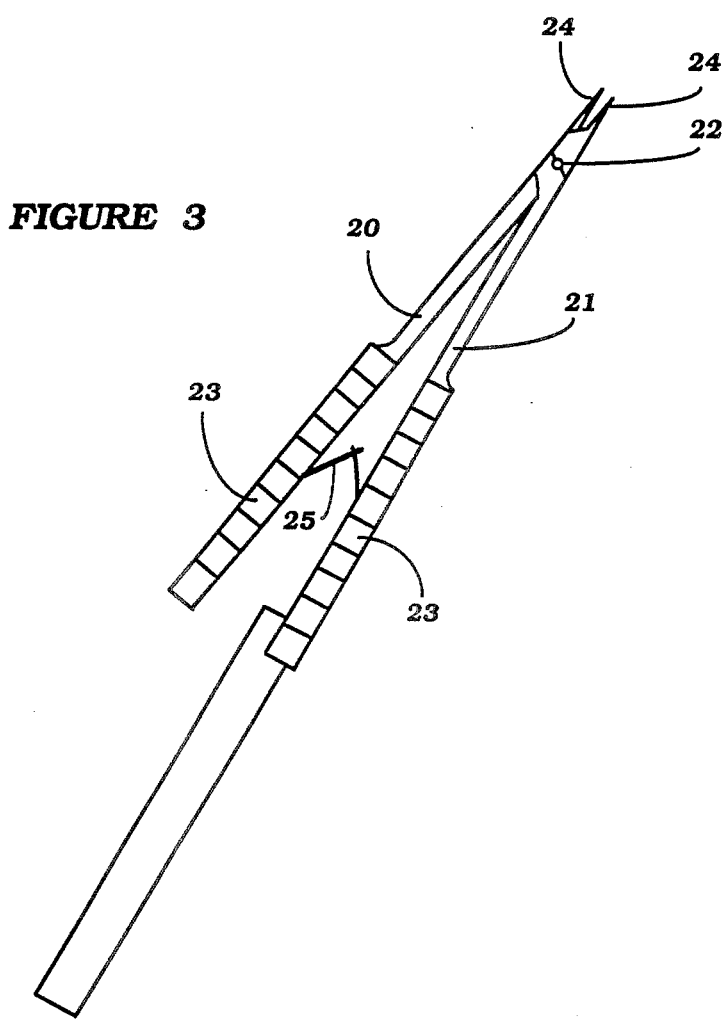
FIG. 3 is a side view of an applying instrument for the blood vessel aneurysm clamp depicted in FIGS. 1 or 2, with said clamp shown in relative size to said applying instrument.

An applying instrument used to apply the clamp is shown in FIG. 3 and generally comprises a pair of arms 20 and 21, which are pivotally connected at a pin 22 such that when the handle portion 23 of the arms 21 and 22 operated together the actuating ends 24 of the arms are expanded. The actuating ends 24 may have recesses corresponding to the pins or rivets provided on the operational ends of the clamp or alternatively have pins or other elements to engage recesses or bores formed in the operational ends, as the case may be, permitting pivotal movement of the clamp with the application instrument. These elements are used to engage the clamp. The handle portions 23 are biased by spring means 25 and may be positioned selectively to retain a clamp in an engagement with the actuating ends 24.

We claim:

1. A clamp for clamping blood vessels or aneurysms to cease blood flow therethrough, either temporarily or permanently, comprising a pair of arms each having a hemostatic end and an opertional end, said arms having a mirror image configuration and being pivotally mounted one to the other such that said arms cross over each other at the pivot point so the hemostatic ends of said arms align with and oppose one another and the operational ends of said arms align with and oppose one another, said hemostatic ends opening relative to one another when said operational ends are similarly opened, and means for biasing said arms to apply clamping force between said hemostatic ends of said arms, said operational ends of said arms having means for securing said clamp to an application instrument so said clamp is held by said instrument and permitted to pivot relative to said application instrument, said clamp being operated by spreading the operational ends of said clamp arms to open said hemostatic ends for application of said clamp to a blood vessel or aneurysm, and then released to provide clamping force thereto.

2. A clamp according to claim 1 wherein said spring means comprises a u-shaped spring disposed between said operational ends of said arms.

3. A clamp according to claim 2 wherein said spring means is attached to a portion of the operational ends of said arms.

4. A clamp according to claim 3 whereby said means for securing said clamp to an application instrument comprises a rivet having a head thereof disposed on inward portion of the operational end of said arms, said rivet attaching said spring means to said arm and providing means for securing said clamp to an application instrument.

5. A clamp according to claim 1 wherein said means for securing said clamp to an application instrument comprises a pin shaped element formed on an inwardly directed portion of said operational end of said arms.

6. A clamp according to claim 1 wherein said means for securing said clamp to an application instrument comprises a spherically shaped element formed on an inwardly directed portion of said operational end of said arms.

7. A clamp according to claim 1 wherein said means for securing said clamp to an application instrument comprises a pyramid shaped element formed on an inwardly directed portion of said operational end of said arms.

8. A clamp according to claim 1 wherein said means for securing said clamp to an application instrument comprises a spherically shaped element formed on an inwardly directed portion of said operational end of said arms.

9. A clamp according to claim 1 wherein said means for securing said clamp to an application instrument comprises a recessed shaped element formed on an inwardly directed portion of said operational end of said arms.

10. A clamp according to claim 1 wherein said means for securing said clamp to an application instrument comprises a opening formed in an inwardly directed portion of said operational end of said arms.

* * * * *